United States Patent [19]
Slamon et al.

[11] Patent Number: 5,846,749
[45] Date of Patent: Dec. 8, 1998

[54] QUANTITATIVE MEASUREMENT OF TISSUE PROTEIN IDENTIFIED BY IMMUNOHISTOCHEMISTRY AND STANDARDIZED PROTEIN DETERMINATION

[75] Inventors: Dennis J. Slamon, Woodland Hills; Michael F. Press, Manhattan Beach, both of Calif.

[73] Assignee: The Regents of the University of California, Oakland, Calif.

[21] Appl. No.: 321,688

[22] Filed: Oct. 12, 1994

[51] Int. Cl.⁶ .......................... G01N 33/53; G01N 33/574
[52] U.S. Cl. .......................... 435/7.23; 435/7.9; 435/7.92; 435/363; 435/7.21; 436/63; 436/64; 436/813
[58] Field of Search .................................. 435/7.21, 7.23, 435/7.9, 7.92, 240.2, 363; 436/63, 64, 813

[56] References Cited

U.S. PATENT DOCUMENTS

| | | |
|---|---|---|
| 4,741,043 | 4/1988 | Bacus . |
| 4,885,238 | 12/1989 | Reddel et al. ............................. 435/29 |
| 5,008,185 | 4/1991 | Bacus .................................... 435/7.23 |
| 5,109,429 | 4/1992 | Bacus et al. . |
| 5,202,931 | 4/1993 | Bacus . |

OTHER PUBLICATIONS

Czerniak et al., *The Journal of Histochemistry and Cytochemistry*, vol. 38, No. 4, pp. 463–466, 1990.

M.F. Press, et al., "Her–2/neu Expression in Node–negative Breast Cancer: Direct Tissue Quantiation by Computerized Image Analysis and Association of Overexpression with Increased Risk of Recurrent Disease," Cancer Research 53, 4960–4907, Oct. 15, 1993.

Primary Examiner—Toni R. Scheiner
Attorney, Agent, or Firm—Richard F. Trecartin; Mark T. Kresnak; Flehr Hohbach Test Albritton and Herbert LLP

[57] ABSTRACT

Cellular components are quantitated using stained cell samples, computerized image analysis, and cellular standards, where the computerized image analysis value can be translated into the amount of the component per cell. The methodology is demonstrated with breast cancer cells and quantitation of the HER-2/neu gene. The quantitation is shown to have prognostic capability as to the future course of the disease.

12 Claims, No Drawings

QUANTITATIVE MEASUREMENT OF TISSUE PROTEIN IDENTIFIED BY IMMUNOHISTOCHEMISTRY AND STANDARDIZED PROTEIN DETERMINATION

This invention was developed at least in part by funding under Grant No. CA36827 and from NCI Grant Nos. CA48780 and CA50589. The government may have an interest in this invention.

INTRODUCTION

1. Technical Field

The field of this invention is the quantitative determination of compounds of interest in cells.

2. Background

As the ability to manipulate cells, relate the characteristics of the cells to status and function, and to associate various markers with physiological indications, there has been an expanding need to be able to obtain semi-quantitative or quantitative amounts of cellular components and their relationships to other cell types. For example, in trying to understand proliferation and differentiation, the processes may involve, not only different proteins, but also different amounts of the same protein. To be able to define the status of a cell during its various stages of proliferation based on markers which vary in concentration could be very valuable in determining the degree of synchronization of a cell population, the interactions between different components in the cell as the cell passes through the various stages before mitosis or meiosis, and the relevant interactions between the different components. In the case of differentiation, by being able to determine levels of various components in the cell, one may identify variations in concentration of the components in relation to the dedication of the cell to different lineages or maturation programs.

Not only will a more quantitative determination of cellular components be useful in research, but such capability can also have diagnostic significance. Increasingly, it is found that cancer prognosis can be related to the level of particular cellular components. For example, the level of oncogenes, receptors, components associated with proliferation, components associated with proliferation repression, and the like can be markers for aggressiveness, metastasis, responsiveness to various therapies, and the like.

There is therefore substantial interest in being able to provide methods which can reproducibly provide reliable quantitative or semi-quantitative data to be used in the understanding of physiological processes, particularly cellular processes, for predictive capabilities of disease progress, disease responsiveness to therapy, cancer aggressiveness, and the like.

Relevant Literature

Press, et al., Cancer Research 53, 4960–4970 (1993) describe the use of computerized image analysis for relating overexpression of HER-2/neu in node-negative breast cancer as an indicia of increased risk of recurrent disease. U.S. Pat. Nos. 4,741,043; 5,109,429 and 5,202,931 describe image analysis systems for detection and quantitation of cellular components, particularly nucleic acids, hemoglobin, and nuclear antigens.

SUMMARY OF THE INVENTION

Methods and compositions are provided for quantitating a molecular cellular component, particularly proteins, on a cellular basis employing immunohistochemical staining and cellular standards to define quantitatively the amount of the cellular component per cell. A cell sample is provided for computerized image analysis by fixing the cells to a support, contacting the cellular sample with a labeled binding member under conditions which provide for an amplified signal per component molecule, detecting the signal level by means of the computerized image analysis and relating the signal level to an amount of component per cell by use of the standards. Kits are provided comprising a plurality of cells having different levels of expression of the component for serving as controls and defining the relationship of the observed signal to the amount of component present.

DESCRIPTION OF THE SPECIFIC EMBODIMENTS

In accordance with the subject invention, methods and compositions are provided for quantitating a cellular component in an amount per cell in relation to a substantially homogeneous cell population. In accordance with the subject method, a cellular sample is employed, which allows for identification of cells of similar characteristics by computerized image analysis, immunohistochemical staining is employed for providing a spectrophotometric signal capable of quantitation by computerized image analysis, and standards are employed to relate the spectrophotometric signal to a quantitative amount of the cellular component on an individual cell basis.

Any cellular component can be quantitatively determined for which an appropriate binding member, usually a receptor, is available. Binding members may take many forms, such as antibodies, particularly monoclonal antibodies, and binding fragments thereof, e.g. Fv, Fab and $F(ab')_2$, lectins, enzymes, surface membrane and cytosolic binding proteins, or ligands, where the ligand specifically binds to the cellular component. Ligands are a special case, where there is a cell component to which the ligand specifically binds. For the most part, the cellular component will be a binding member, particularly a surface membrane protein receptor, or may be a protein in the cytosol, or a protein associated with an organelle, internal to the organelle or in the membrane of the organelle, where the organelle would be a nucleus, mitochondrion, or the like, or associated with an internal membrane, such as the endoplasmic reticulum. Of particular interest are cellular components associated with the surface membrane and the cytosol.

Besides proteins, other components of interest include sugars, by themselves or in combination with other compositions, e.g. proteins, such as glycoproteins and proteoglycans, and lipids.

The amount of the component should be sufficient to allow for a differential signal between two different states of the cell, so as to allow for discrimination of the state of the cell. Usually, the amount of the component will be at least about 10 fg per cell, more usually at least about 0.5 pg per cell.

The cells of interest may be any type of mammalian cell, particularly primate, more particularly human. Depending upon the purpose of the quantitation, the cells may have various stages of differentiation, and may be normal, precancerous, or cancerous, may be fresh tissue, dispersed cells, immature cells, including stem cells, cells of intermediate maturity, and fully matured cells. The cells may be derived from various organs and tissues, including hematopoietic cells, muscle cells, fibroblasts, lung cells, liver cells, cardiac cells, neuronal cells, breast cells, prostate cells, bone cells, kidney cells, mucosal cells, epithelial cells, skin cells, endothelial cells, lymph node cells, thymus cells, endometrial cells, ovarian cells, gastrointestinal tract cells and the like.

By employing the subject invention, numerous questions can be asked concerning the cells, particularly as to distribution of proteins and their relationship to the various stages of the cell and the relationship of the distribution to normal, pre-cancerous and cancerous states.

The sample for assaying may be prepared in a wide variety of ways, depending upon the nature of the cells or tissue, convenience, the purpose for the quantitation, the homogeneity or heterogeneity of the cells, the stability or fragility of the cells, etc.

Techniques which may be used to prepare the sample include cytospins, cell pellets, paraffin-embedded sections, or other specimens that have been frozen or formalin-fixed, and the like. The number of cells involved will usually be at least about 1,000. For neoplastic solid tissue, usually a biopsy will be the source of the tissue. Depending upon the manner of preparation of the sample, there may be differences in the observed signal. Therefore, one method of preparing the sample will be preferred over another, depending upon the level of signal over the range of interest. For example, paraffinized tissue may provide for lower levels of immunostaining than frozen tissue. For tissue, usually the sample will have an area of equivalent size to from about 0.2 cm to 2.0 cm in diameter. The methods of preparing the sample are well known and have been amply described in a wide variety of texts and papers. See, for example, Theory and Practice of Histotechnology by Dezna Sheehan and Barbara Hrapchak; and Diagnostic Cytopathology by Leopold Koss.

The prepared sample may then be combined with a labeled binding composition comprising a specifically binding probe for immunohistochemical detection. Various labels may be employed which provide for spectrophotometric detection, particularly fluorescers, or enzymes which produce a product which absorbs light or fluoresces, preferably fluoresces. A wide variety of labels are known which provide for strong signals in relation to a single binding event. Fluorescent molecules which may be used include intercalated staining dyes in DNA chains, such as are described in U.S. Pat. No. 5, 321,130, phycoerythrins, fluorescein, rhodamine, Texas red, or enzymes which provide for colored dyes or fluorescers, which enzymes include hydrolases, e.g. phosphatases and glycosidases, oxidoreductases, such as peroxidases, oxidases, NADH dependent enzymes, etc. Enzyme dye combinations include alkalaine phosphatase/CAS red, hroseradish peroxidase/ diaminobenzidine, amino ethylcarbazole, chloronaphthol and the like. The method of preparing conjugates of fluoresces and proteins, such as antibodies, is extensively described in the literature and does not require exemplification here.

Further amplification can be achieved by using combinations of specific binding members, such as antibodies and anti-antibodies, where the anti-antibodies bind to a conserved region of the target antibody probe, particularly where the antibodies are from different species, specific binding ligand-receptor pairs, such as biotin-streptavidine or avidin, or polyvalent ligand and monoclonal antibodies, homologous nucleic acid sequences, and the like. Thus, one effectively builds a sandwich of binding members, where the first binding member binds to the cellular component and serves to provide for secondary binding, where the secondary binding may or may not involve a label, and may further provide for tertiary binding where the tertiary binding will provide a label. The sample is brought in contact with a solution of the binding members, where the binding members may be added consecutively or concurrently, depending upon the nature of the binding members. Usually, the binding probe will be added first, allowed to incubate, usually not more than about 30 min, followed by the other members of the binding composition, where incubations of 30 min or less may be employed. When added consecutively, after each addition, the sample may be washed to remove any non-specific binding member, using conventional buffered wash solutions as washes, where one or more washes may be involved.

Standard cell compositions are also provided, where the standard cells may be of the same or different species, cell type, level of maturity, or the like. At least two different cell compositions will be employed having differing amounts of the component of interest. Preferably, three or more cell compositions will be employed, rarely more than ten to provide for different levels of the component of interest within the desired range. Depending upon the nature of the cells, they may be treated in the same or different manner in the preparation of the sample, preferably in the same manner. For example, where biopsies from tumors are employed, one may obtain samples from normal tissue and tumerous tissue and/or cell lines, and analyze the various tissues and cell lines for the level of the cellular component, as well as determining the signal obtained using immunohistochemical staining in substantially the same manner as was performed with the sample. Desirably, the cells which are employed will be the same types of cells which comprise the sample, as to species, lineage, differentiation, and general characteristics, and will have been treated in substantially the same way as the sample in the immunohistochemical staining. For the most part, the control cells will be immortalized, either naturally occurring by transfection with viruses, oncogenes or the like. However, if one changes the procedure or uses different types of cells, one may standardize the standards by using a single comparison of a standard cell composition and a sample cell composition, where the amount of the component of interest is determined by a rigorous method. All of the values obtained from the standard compositions may then be normalized based on the values obtained in the direct comparison. Besides using cells from naturally occurring sources, one may also use modified cells, where an expression construct comprising a gene(s) providing the component of interest is introduced into cells, where the resulting modified cells provide for a range of amounts of the component of interest. This can be achieved by using different dosages of the gene, particularly when one has an extra chromosomal element, where the copy number can be controlled, by providing for a transcriptional initiation region which can be controlled, so as to provide for varying degrees of transcription, by using different genetic constructions with different cells, and by cloning cells and segregating cells having different levels of expression of the component of interest. All of these techniques are well known in the literature and procedures for their performance may be found in Molecular Cloning: A Laboratory Manual, eds. Sambrook et al., Cold Spring Harbor Laboratories, Cold Spring Harbor, N.Y., 1988. The cells may then be screened to determine the level of the component of interest present by various techniques.

A wide variety of assays may be used to detect the component of interest. Particularly, where the component of interest is a protein, one may use Western blot analyses of lysates from about $10^4$ to about $10^8$, preferably about $10^6$ cells of each cell type, where each of the cells provides about the same amount of the component of interest.

To quantitate the amount of the component of interest, a pure sample of the component of interest is prepared and a series of dilutions prepared for comparison with the lysate obtained from the cellular standard. The purified component of interest may be obtained by any convenient means, depending upon the nature of the component, whether it is commercially available, whether there are known methods of isolation and purification, or the like. By employing SDS-PAGE and Western blot with proteins, the protein band can be compared with the various diluted amounts of the pure protein. For example, densitometric scanning and gamma counting of the excised bands may be employed. These assays may be carried out at about the same time as the immunohistochemistry assay, so that one has a direct correlation between the amount of protein present in the cells per cell and the optical signal observed with the immunohistochemical staining. One can then prepare a quantitation curve relating the signal observed with the immunohistochemical staining and the amount of protein present in the standard cells. Alternatively, one may use a standard curve to be used with a plurality of determinations, where the curve is determined by at least two, usually at least three or more determinations. Instead of the above assay, one may use immunoassays, where directly or indirectly, labeled binding member, e.g. antibody, specifically binding to the component of interest is employed. Numerous assay protocols are available, such as RIA (a radioisotope labeled binding member); ELISA (an enzyme labeled binding member); FIA (a fluorescer labeled binding member); etc., where the component of interest may be determined. Where such assay is not commercially available, the reagents and protocol may be readily developed in accordance with known procedures. The signal obtained from the lysate of the cellular composition, with or without enrichment of the component of interest, may be related to a concentration curve relating signal to concentration of the component of interest obtained with known amounts of the component of interest.

If desired, one may also carry out a nucleic acid staining of the cells. The nucleic acid staining serves to identify individual cells, to indicate whether the nucleus is normal or aberrant, presence of chromosomal aneuploidies or translocations, and determine the amount of DNA per cell.

To determine the signal from the immunohisto-chemical staining, various commercially available apparatuses may be employed conveniently, computerized imaging systems, such as the CAS 200 computerized imagining system (Cell Analysis Systems, Inc., Elmhurst, Ill.). These companies frequently supply reagents for the immunostaining of the samples. The sample or samples of interest may be examined in conjunction with the controls or standards or a standard curve may be prepared and used with subsequent determinations of samples. In the latter case, it is desirable to repeat the standardization process on a sufficiently frequent basis, so as to insure that the system of reagents and staining is working properly. The data obtained with the samples can be directly correlated with the curve defining the signal from the immunostaining with the amount of component per cell. In this way, various components may be quantitated, so as to provide for discrimination between various cells, which might otherwise appear to be the same. With the subject invention, one can detect changes in concentration of individual components of the cell in relation to other components and in relation to the characteristics of the cell and the cell's function. One or more micros may be scanned, usually 2 to 10 fields, and the results averaged or added to provide a sufficient number of cells being determined for the quantitation. A microscopic field will generally have an area of approximately 500 square microns.

As a convenience, kits may be provided which might include at least two vials, usually at least three vials comprising viable cells which produce known amounts of the component of interest. By employing stable cell lines, the cells may be grown up and expanded to provide fresh cultures for use as standards, where the standards may be used in conjunction with sample determination. Alternatively, the cellular acomposition may be fixed to a solid support. Slides may be pre-prepared of standardized cells of known amount of the component of interest, so that the slides may be stained in the same manner as the sample and the immunostaining signals compared directly with the controls of known component amount. In addition, staining dyes may be supplied with appropriate binding member probes, particularly antibodies, which bind to the component of interest, where such binding member probes may be labeled or be used in conjunction with other labeled components which bind to the binding members including the probe, as described previously. In addition, one may provide reagents associated with immunoassays, where the probe will be an antibody, poly- or monoclonal and may be labeled with a radioisotope, enzyme or fluorescer, or an anti-probe may be provided, which is labeled, or one may provide for the aggregation of the anti-probe, by having a third binding member, which binds to the labeled antiprobe. Alternatively, one may provide for the antiprobe to be unlabeled and have a third binding member binding to the antiprobe, which third binding member is labeled. One might consider an antibody probe, a biotin labeled antiprobe and enzyme or fluorescer labeled streptavidin.

The following examples are offered by way of illustration and not by way of limitation.

EXPERIMENTAL

Materials and Methods

Patient Material

This investigation, involving human subjects, was reviewed and approved by the Institutional Research Boards of all involved laboratories.

"Relapse"–"No-Relapse" Study. The study sample was selected from 704 node-negative invasive breast carcinoma (infiltrating ductal or lobular carcinoma) cases diagnosed between 1971 and 1982 in Alberta, Canada. Patients having a diagnosis of breast carcinoma in situ only were excluded. The records of these patients were maintained in a computerized population-based registry by the Breast Unit of the Cross Cancer Institute. The recurrence rate of the 704 women was estimated to be 18 and 28% at 5 and 10 years, respectively, on Dec. 31, 1987 (Paterson et al. [1991] *Cancer Res.* 51:556–567). For this study, all 105 cases with known menopausal status at first treatment who experienced a local recurrence or metastasis before Dec. 31, 1987, and for whom archival tissue was available were paired with controls, from the same cohort, who had not experienced a local recurrence or metastasis before Dec. 31, 1987, and who had been disease free for at least as long as their matched "case." For ease of reference we will often refer to patients with relapse as "cases" and their matched nonrelapsed (disease-free) patients as "controls." Node negativity was based on sampling of at least four axillary lymph nodes in all cases and controls (cases: range, 4–27, mean, 10; controls: range, 4–29; mean=11). Seventy-four % of the cases and controls had seven or more axillary lymph nodes sampled. These cases and controls were matched for menopausal status (35 premenopausal, 4 perimenopausal, 66 postmenopausal pairs), and age at treatment (within 5 years). They were then hierarchically matched as closely as possible with respect to size of the primary tumor (T category, International Union Against Cancer), estrogen receptor status (positive, negative, unknown), and anniversary year of diagnosis (within 3 years). A total of 90.5% of cases were matched on all of these criteria with their controls. Distribution of primary tumor size in the cohort was as follows; 31.9% were T1A; 1.0% were T1B; 55.7% were T2A; 5.2% were T2B; 4.8% were T3A; and 1.4% were T3B. The ages of the women included in the study were: 5, 20–29 years old; 13, 30–39 years old; 58, 40–49 years old; 52, 50–59 years old; 56, 60–69 years old; 22, 70–79 years old; and 4, 80–89 years old. The median follow-up time for both cases (range, 60–168 months) and controls (range, 60–192 months) was 108 months. The case-control approach was adopted to maximize the efficiency of obtaining blocks. Although some additional statistical power would have been obtained if all cases with known menopausal status had been included, the 105 case-control pairs studied provided more than sufficient statistical power to test the relationship between HER-2/neu expression and relapse.

Almost all of these node-negative breast cancer patients were treated with modified radical or total mastectomy. Two were treated by segmental resection. Twenty of the 210 women (10 cases and 10 controls) received adjuvant radiation therapy. None had primary chemotherapy or hormonal therapy. Elimination of the 20 patients who received adjuvant radiation therapy had no effect on the conclusions of this study. As a result of the health care system in Canada, almost all patients with a given disease are treated at one of a few regional centers. This circumvents the potential lack of uniformity in treatment and follow-up inherent to multiinstitutional group studies.

Immunohistochemical Staining

HER-2/neu Antibodies. A rabbit anti-HER-2/neu polyclonal antiserum (R60) directed against the HER-2/neu gene product has been previously described and was used in this study (Slamon et al [1989] *Science* 244:707–712, Slamon et al [1989] *Cancer Cells* 7:371–380). This antiserum has no cross-reactivity with epidermal growth factor receptor and was used to identify HER-2/neu oncoprotein in tissue sections as described previously (ibid). The 3B5 monoclonal antibody directed against a similar epitope was generously provided by Dr. Marc van de Vijver, and was also used to evaluate HER-2/neu expression immunohistochemically (Van de Vijver et al. [1988] *New Engl. J. Med.* 319:1239–1245).

Sensitivity and Specificity of Immunostaining for HER-2/neu Overexpression. Ninety fully molecularly characterized primary breast carcinomas, from a group of 187 previously studied samples, evaluated at the DNA, RNA, and protein levels for HER-2/neu alteration (Slamon et al [1989] *Science* 244:707–712), were used as standards to determine both the sensitivity and specificity of our immunostaining reagents and methods in the paraffin-embedded sections used in this study. These standards were comprehensively characterized as follows: degree of HER-2/neu gene amplification was determined by Southern blot analysis of EcoRI digested tumor tissue DNA (ibid); the relative amount of HER-2/neu mRNA was determined by Northern hybridization of total RNA (ibid); and the relative protein content was determined by Western immunoblot analyses of tissue extracts as well as immunohistochemical staining of tissue sections (ibid).

In the context of this report "low expression" and "overexpression" is used to refer to the amount of HER-2/neu RNA or protein present in a breast cancer, whereas "immunostaining" is used to refer specifically to the HER-2/neu membrane staining identified by immunohistochemistry. The studies with frozen tissue samples (ibid) provide a measure of HER-2/neu gene expression at the RNA and protein levels in the breast cancer standards. The amount of HER-2/neu gene expression, with few exceptions (10%), is proportional to the number of copies of the gene in tumor cells (ibid). Most breast cancers with no increase in the HER-2/neu gene copy level relative to a control gene on the same chromosome (unamplified or single-copy cases) have a detectable, but low amount of HER-2/neu RNA and protein. This "low expression" can be identified in frozen tissue sections by immunohistochemistry as weak membrane immunostaining. The low level of protein expression is usually not identifiable as membrane immunostaining when the tissue is formalin fixed and processed for paraffin embedding (Press et al. [1990] *Oncogene* 5:933–962). Breast cancers with an increase in the number of HER-2/neu gene copies relative to a control gene on the same chromosome have gene amplification. Amplification is measured in multiples of the control gene content (2→5-fold increased). Breast cancers with HER-2/neu amplification have increased levels of gene expression, referred to as "overexpression." Overexpression is identified immunohistochemically as membrane immunostaining which is stronger than that observed in breast cancers lacking amplification (Slamon et al [1989] *Science* 244:707–712) and stronger than that observed in normal adult tissues (Press et al, supra). A few breast cancers used as standards had overexpression of HER-2/neu without having gene amplification by Southern blot (see below).

The 90 standards for the current study were selected so that 45 of them contained a single copy of the gene and expressed low levels of the protein while the other 45 had evidence of HER-2/neu overexpression. Thirty-three of these latter samples were amplified to varying degrees while 12 contained overexpression in the absence of measurable gene amplification. Relative immunostaining levels, determined in a blinded fashion by immunohistochemistry of paraffin-embedded tissue sections, were compared to the molecular findings from this group of 90 standards. Immunostaining for HER-2/neu with the 3B5 monoclonal antibody was also performed both as described above and by the avidin-biotin-chromogen technique previously described (Van de Vijver, supra).

Evaluation of Cases and Controls. Tissue sections, 4 $\mu$m thick, from formalin-fixed, paraffin-embedded blocks of relapse cases and disease-free controls were evaluated for HER-2/neu protein expression by immunohistochemistry. This was done blinded to all clinical information regarding the samples being analyzed. Positive and negative immunostaining test tissue sections were included with each immunohistochemical procedure. The sites and intensity of immunoprecipitate formation were identified microscopically following treatment with the chromogen 3,3'-diaminobenzidine. Immunostaining was scored nonquantitatively as low immunostaining [negative(−) or weak immunostaining, i.e., slightly detectable immunostaining in isolated cells] and intermediate or strong immunostaining according to the relative intensity of membrane staining. The sensitivity and specificity of the immunostaining procedure was determined in the 90 known breast cancer standards as follows: sensitivity=true positives/true positives+false negatives; specificity=true negatives/true negatives+false positives.

DNA extracted from punch biopsies of the paraffin blocks from the cases and controls were assayed independently by slot blot analysis to determine HER-2/neu gene copy number as described elsewhere (Paterson, supra). DNA obtained from paraffin embedded tissue is of variable quality and is, in general, not intact. Since the quality of the DNA obtained from paraffin-embedded tissue is less than that obtained from frozen tissue, the distinction between lower copy numbers is more difficult to make. Although a 2-fold amplification level can be readily distinguished in DNA from frozen tissue (Slamon et al [1989] *Science* 244:707–712), the fluctuation in DNA size obtained from paraffin-embedded tissue can influence probe signal intensity; consequently, only gene copy values of 3-fold or greater were regarded as distinguishable from single copy for the slot blot analyses included in this study (Paterson, supra).

Quantitative Determination of HER-2/neu Protein Content

Cell Lines. A series of established and molecularly engineered cell lines expressing HER-2/neu protein levels, ranging from low to high, were used for quantitation of HER-2/neu in tumor cells. The established cell lines included MCF-7, SK-BR-3, CAOV3, MDA-MB-231, and NR6. All of these cell lines were of human origin except NR6 (Prus et al [1977] *P.N.A.S.* 74:3918–3921) and were obtained from the American Type Culture Collection. The molecularly-engineered cell lines were all derived from these established lines. The engineered and matched control cell lines were developed by infecting the cells containing a single copy of the HER-2/neu gene and expressing low levels (1+) of the protein with a retroviral expression vector either containing or lacking the HER-2/neu cDNA, respectively. In brief, the coding region from a full-length cDNA of the human HER-2/neu gene (Slamon et al [1989] *Science* 244:707–712) was inserted into the retroviral expression vector pLPNSN-2 (Osborne et al [1988] *P.N.A.S.* 85:6851–6855). In this vector the HER-2/neu cDNA is transcribed from a Moloney murine leukemia virus promoter and a neomycin phosphotransferase gene (neo) is transcribed from an internal SV40 promoter. A similar vector expressing neo but without the HER-2/neu cDNA (pLXSN) was used as a control (Miller and Rossman [1989] *BioTech.* 7:980–990). Retroviral packaging and infections were performed as described previously (Miller and Buttimore [1986] *M.C.B.* 6:2895–2902).

Quantitation of HER-2/neu protein content in both the established and engineered cell lines was performed using Western blot analyses of lysates from $10^6$ cells of each of the above cell lines. The Western analyses were performed simultaneously and on the same blot with known amounts of a recombinantly expressed, purified protein fragment comprising 80% of the HER-2/neu amino acid sequence. This purified HER-2/neu protein fragment is recognized by the R60 antibody. Protein preparation and isolation was accomplished by expressing a fragment of the HER-2/neu gene encoding 80% of the amino acid sequence beginning at the amino terminus. An NcoI-KpnI restriction fragment from the coding region of the human HER-2/neu cDNA was inserted into an *Escherichia coli* expression vector containing a λpL promoter. Expression was induced by a temperature shift during fermentation. The HER-2/neu protein fragment was expressed as a fusion protein to 18 amino acids from the $NH_2$-terminal sequence of the *E. coli* trp E protein. Following induction, the HER-2/neu fragment accumulated in inclusion bodies which represented approximately 5% of the total bacterial protein. Purification of the recombinant HER-2/neu protein fragment was performed by an inclusion body isolation followed by gel filtration chromatography. *E. coli* paste, stored frozen at −70° C., was thawed and resuspended in 25 mM Tris (pH 7.5)–100 mM NaCl–0.2 mM phenylmethylsulfonyl fluoride, with 1 mg/ml lysozyme. After incubating for 2 hours on ice, the suspension was frozen at −70° (and rapidly thawed in a water bath. DNase I and $MgCl_2$ were added to final concentrations of 20 µg/ml and 2 mM, respectively, to reduce the viscosity of the lysate, and insoluble material was collected by centrifugation (10,000×g, 30 min). The pellet was resuspended in 25 mM Tris(pH 7.5)–100 mM NaCl–1.0% (v/v) Nonidet P-40 and centrifuged again (10,000×g, 30 min) . The final pellet was dissolved by boiling for 3 min in 25 mM Tris(pH 7.5)–1% w/v SDS, 1 mM dithiothreitol. 1 ml of the solubilized inclusion body fraction was loaded on a 1.6×50 cm Superose 6 column (Pharmacia LKB) and eluted with 25 mM Tris(pH 7.5)–100 mM NaCl–0.1% (w/v) SDS at a flow rate of 0.2 ml/min. Fractions containing the HER-2/neu protein fragment were identified by SDS-polyacrylamide gel electrophoresis and Western blot and subsequently pooled and stored frozen at −70° C. The concentration of the purified HER-2/neu protein fragment was determined using a bicinchoninic acid protein assay (Pierce) standardized with bovine γ-globulin (Bio-Rad).

Dilutions of purified protein were used to prepare calibration curves with quantities ranging from 20 to 80 ng of protein. The resulting bands on Western blot were than quantitated by both densitometric scanning and gamma counting of the excised bands representing the HER-2/neu signals obtained from the lysates of each cell line to determine the relative amount of HER-2/neu protein/$10^6$ cells. Simultaneous with preparation of cell lysates was preparation of cytospins and pellets from the same culture flask of each cell line. The cell pellets were frozen in OCT cryosectioning media and 4-µm frozen sections were prepared. Cytospun cells were washed in buffer and fixed immediately. Immunostaining was performed as described below. The relative absorbances of cell immunostaining was determined with computerized image analysis and compared to the levels of HER-2/neu, determined by quantitative Western blot analysis. The relative homogeneity of HER-2/neu staining found in the various cell populations allows for determination of the average amount of HER-2/neu protein per cell.

Computerized Image Analysis of HER-2/neu Immunostaining. Quantitation of HER-2/neu immunostaining was performed using a CAS 200 computerized imaging system (Cell Analysis Systems, Inc., Elmhurst, Ill.), calibrated with cells from the above procedures and tissues immunohistochemically stained for this purpose. In order to permit simultaneous measurement of HER-2/neu immunostaining and DNA content in individual tumor cells, the samples were immunostained by an alkaline phosphatase anti-alkaline phosphatase technique using a red chromogen (CAS red; CAS, Inc., Elmhurst, Ill.) and counterstained for DNA with feulgen stain (cyanin blue; CAS, Inc.). Optimal conditions for alkaline phosphatase anti-alkaline phosphatase were similar to those determined for the phosphatase anti-phosphatase technique. Fixation for HER-2/neu immunostaining combined with Feulgen counterstaining was performed in 95% ethanol for 10 min followed by 10% neutral buffered formalin for 30 min. Tissue sections from breast cancers and from cytospun cells were incubated with HER-2/neu antiserum (R60, 1:1000 dilution; 1 h), followed by a mouse anti-rabbit antibody (The Jackson Laboratory; 10 mg/ml, 30 min), a goat anti-mouse antibody (BRL; 10 mg/ml, 30 min), and finally a mouse monoclonal alkaline phosphatase anti-alkaline phosphatase antibody (Dako; 1:80 dilution, 30 min). Each of these antibody incubations was followed by three 5-min-rinses in Tris-buffered saline. The site of the immunoprecipitates was identified with a naphthol derivative and a diazonium coupler, CAS red (CAS, Inc.). Counterstaining of nuclear DNA was performed with a Feulgen stain as per instructions of the manufacturer (CAS, Inc.).

Statistical Methods

Averages and standard errors of HER-2/neu protein content of breast cancers were calculated using a random effects model with each patient's HER-2/neu protein content serving as the basic data. Standard statistical methods for the analysis of matched case-control studies were used for the analysis of risk of relapse related to HER-2/neu expression (Breslow et al [1980] *Statistical Methods in Cancer Research*, Vol. 1). Trends for ordered variables were assessed by the score test using both continuous and categorized forms. Multivariate logistic regression for matched studies was used to adjust the results for the other risk factors which had significant effects.

Quantitative Western immunoblot and immunostaining by alkaline phosphatase anti-alkaline phosphatase technique for HER-2/neu oncoprotein was demonstrated in established and engineered cell lines. Quantitative Western immunoblot analysis of HER-2/neu expression was determined in the following cell lines: NR6/10, NR6, SK-BR-3, MCF-7, M6/10, Ca-Ov-3, C7/10, MDA-MB-231, and MDA-MB-231+HER-2. The high expressing cell lines NR6/10, M6/10, C7/10 and MDA-MB-231+HER-2 were produced by transfection with a vector containing the entire coding region of the HER-2/neu gene. Low expression cell lines (NR6, MCF-7, Ca-Ov-3, MDA-MB-231) were produced as controls by transfection with a vector lacking the HER-2/neu gene. SK-BR-3 is an established breast cancer cell line with amplification and overexpression of HER-2/neu genes.

Lanes to which were added 20, 40, 60 and 80 mg of labeled HER-2/neu protein were prepared for Western analysis, where the protein was recombinantly produced in bacteria using an expression vector containing 80% of the coding region of the HER-2/neu cDNA and purified to homogeneity as described above. The lanes containing dilutions of the purified HER-2/neu oncoprotein were quantitated by scanning with soft laser densitometry of the autoradiogram as well as by direct measurement of the radioactivity associated with the p185 band in the gel in a gamma counter. The area counted was excised from the gel. These two approaches established a quantitative calibration curve for the HER-2/neu protein product. The p185 HER-2/neu bands were quantitated identically for each of the cell lines.

Comparison of the determined values with the calibration curve permitted determination of the amount of HER-2/neu oncoprotein identified in each cell line. Since the total protein loaded into each lane was extracted from $10^6$ cells from each cell line and the cell to cell staining is relatively uniform within a cell line, the amount of protein could be based on a per cell basis. The numerical values shown in the following table are based on this autoradiagram.

TABLE 1

Quantitation of HER-2/neu oncoprotein in cell lines[a]

| Sample | Quantitation of HER-2/neu protein[b] | |
|---|---|---|
| | Western immunoblot | Image analysis |
| NR6-10 | 2.61 | 2.52 |
| NR-6 | 0.40 | 0.20 |
| SK-BR-3 | 2.24 | 2.47 |
| MCF-7 | 0.36 | 0.11 |
| M6-10 | 1.62 | 1.52 |
| CA-OV-3 | 0.41 | 0.20 |
| C7-10 | 1.14 | 1.18 |
| MDA-MB-231 | 0.39 | 0.13 |
| MDA-MB-231-HER-2 | 0.82 | 1.97 |

[a]See FIG. 3 for illustration of the material analyzed. The samples in the table are arranged in the same sequence as the samples in the figure comparing low expression in parental cell lines with high expression in HER-2/neu-transfected cell lines. SK-BR-3 is an established, known high expressor cell line not produced by transfection.
[b]Expressed in pg of protein/cell.

RESULTS

Detection of HER-2/neu Protein in Paraffinized Tissue Sections

The results of immunostaining 90 primary breast cancers for HER-2/neu oncoprotein expression with both the R60 and 3B5 antibodies is shown below.

TABLE 2

Overexpression detected by immunostaining of paraffin-embedded tissue sections from breast cancers with and without amplification of the HER-2/neu oncogene[a]

| Amplification of HER-2/neu oncogene | Level of RNA, p185 expression | Immunostaining in paraffinized sections[b] | |
|---|---|---|---|
| | | Polyclonal R60 (Overexpr by ICA/total) | Monoclonal 3B5 (Overexpr by ICA/total) |
| >5-fold | Overexp | 18/19(95) | 12/19(63) |
| 2-5-fold | Overexp | 7/14(50) | 4/14(29) |
| Single-copy | Overexp | 6/12(50) | 3/12(25) |
| Single-copy | Lowexp | 0/45 | 0/45 |

[a]These breast cancers, used as standards for characterizing the sensitivity and specificity of immunostaining in paraffinized sections, were previously molecularly characterized with regard to HER-2/neu gene copy number and expression. In the original series of 187 cases, from which 90 cases were selected, single copy (i.e. no HER-2/neu amplification) low expression was found in 63%, single-copy overexpression in 10%, 2-5-fold amplification with overexpression in 9%, and >5-fold amplification with overexpression in 18% (29, 54).
[b]Individual breast cancers were evaluated by immunohistochemistry and classified as showing low (Lowexp), intermediate, or high (Overexp) immunostaining. Any degree of distinct membrane staining in the paraffin-embedded tumor cells was considered as demonstrating overexpression (intermediate and high immunostaining groups together). Monoclonal 3B5 immunostained tumor frequently contained coarse cytoplasmic staining either with or without membrane staining in both known overexpressors and in known low expressors. Only membrane staining was considered in evaluating 3B5.

45 samples were molecularly characterized as single-copy, low expressors of HER-2/neu, while 12 were single copy overexpressers and 33 were amplified overexpressors of the protein. The degree of immunostaining with a polyclonal antiserum (R60) was consistently reduced in paraffinized tissue when compared to the frozen tissue from the same breast specimen. However, this was least apparent in the cases with greater than 5-fold amplification of the gene. The characterized-paraffinized breast cancer specimens showed intermediate or high immunostaining of the HER- 2/neu protein in tumor cell membranes in all but one of the cases with >5-fold amplification of the gene. One-half of the specimens (50%) with 2 to 5-fold amplification had intermediate or high immunostaining of tumor cell membranes which was clearly distinguishable from the lack of immunostaining seen in single-copy cases expressing low levels of the protein. In addition, one-half of the single-copy overexpressing breast cancers had intermediate or high expression of tumor cell membranes in paraffin sections. Conversely, none of the single-copy low expression cases showed intermediate or high expression. Therefore in the 90 standards the specificity is 100%. (The data is found in Table 2).

The immunostaining of tumor cells in paraffin sections was not as homogeneous as in frozen sections from the same specimen. Conversely, appropriately fixed, well-preserved breast cancer specimens demonstrated the same uniformity of immunostaining seen in frozen tissue. In specimens where fixative penetration appeared inadequate, the strongest immunostaining was seen at the periphery of the tissue sample where the fixation was more uniform. Similar to frozen tissue, stromal cells, connective tissue, lymphocytes, and normal tissues were not immunostained in paraffin-embedded material.

Based on earlier results, it would be predicted that the polyclonal R60 antiserum would identify approximately 72% of breast cancers with HER-2/neu overexpression in paraffin-embedded section, indicating that nearly thereof every four true overexpressers are detected (sensitivity) and indicating that this antiserum is appropriate for investigation of a large cohort of archival node-negative breast cancers. The results with the 3B5 monoclonal antibody were less successful.

The data in the following table is a comparison of the signals obtained from known amounts of the purified protein with signals obtained from the HER-2/neu protein in lysates of defined numbers of cells from each of the referenced cell lines, which provided for a quantitation curve of the amount of HER-2/neu in each line.

A critical part of this quantitation process was that all referenced cell lines used in the Western immunoblot analyses were simultaneously prepared for immunohistochemistry to circumvent potential problems of variation in HER-2/neu protein content which may occur in cell culture over time. This approach allowed for subsequent calibration of the immunohistochemical staining intensity read by the imaging system based on quantitative data of known HER-2/neu protein content in cells prepared at exactly the same time.

The relative absorbance of HER-2/neu immunostaining was then determined in 5 microscopic fields for each of the characterized cell lines using the computerized image analysis system. This allowed for objective quantitation approaching levels as measured in immunostaining absorbance units and these results could be converted to and reported in PG of HER-2/neu protein per cell based on the Western blot of the same cell lines and the recombinantly expressed purified protein. See the above table. The use of cell lines rather than tissue for preparation of the lysates used in the quantitative Western blots circumvented the previously described problems of delusional artifacts introduced by protein from nonmalignant cell populations found in tissue specimens.

Each of the molecularly characterized breast cancers were immunostained with the alkaline phosphatase anti-alkaline phosphatase technique and counter stained with Feulgen stain. Comparison of formalin-fixed paraffin-embedded cells with quantitative image analysis of alleaquats of the same cells prepared as frozen samples show that the paraffin-embedded cells had an apparent HER-2/neu content which was 61.3% of that observed in sections of the same frozen cells. Assuming that the reduction in immunostaining intensity of breast cancer specimens was close to that observed in similarly treated culture cells, HER-2/neu protein content in fixed tissue sections could be quantitated. The HER-2/neu protein content of breast cancers with >5-fold amplification was 3.38+−0.29 pg/cell(N=20); those with 2 to 5-fold amplification had 2.60+−0.47 pg/cell(N=10); those with overexpression but no amplification had 2.01+−0.73 pg/cell (N=8); and those with neither amplification or overexpression had 0.18+−0.02 pg/cell (N=37). The specimens described in this node-negative case-control study were similarly analyzed. Those which had been categorized as showing low immunostaining had a HER-2/neu protein content of 0.09+−0.012 pg/cell (1+;Table 3), those with an intermediate immunostaining (2+; Table 3), had 2.41+−0.35 pg/cell and those with strong immunostaining (3+; Table 3) had 3.46+−0.44 pg/cell. These results demonstrate that computerized image analysis can be reliably used to quantitate HER-2/neu protein content in tissue sections using immunohistochemistry.

Immunohistochemical Staining of Node-Negative Primary Breast Cancer Study Cohort for HER-2/neu Among the 105 relapsed cases and 105 disease-free controls a total of 62 breast cancers (41 cases, 21 controls) showed intermediate or strong immunostaining by immunohistochemical analyses (Table 3). 25 (20 cases, 5 controls) of the 210 malignancies were found to have oncogene amplification by slot blot analysis of DNA extracted from the paraffinized material and all but one showed intermediate or strong immunostaining by immunohistochemistry. Conversely, 38 malignancies identified as having intermediate or strong immunostaining by immunohistochemistry did not have amplification as determined by slot blot analysis. A single malignancy which had 6-fold amplification of the HER-2/neu gene, but no immunostaining by immunohistochemistry, appeared unique as compared to prior experience. The observed result may have been caused by a tissue fixation problem.

TABLE 3

HER-2/neu immunostaining in 105 case and 105 control node-negative breast cancers

| | Immunostaining for HER-2/neu | | |
|---|---|---|---|
| | Low | Intermediate | High |
| Study cases Gene amplification[a] | | | |
| Single-copy | 63 | 16 | 6 |
| 3-5-fold[b] | 0 | 3 | 3 |
| >5-fold | 1 | 3 | 10 |
| | 64 | 22 | 19 |
| Total = 105 cases Controls Gene amplification[a] | | | |
| Single-copy | 84 | 15 | 1 |
| 3-5-fold[b] | 0 | 2 | 2 |

TABLE 3-continued

HER-2/neu immunostaining in 105 case and 105 control node-negative breast cancers

|  | Immunostaining for HER-2/neu | | |
|---|---|---|---|
|  | Low | Intermediate | High |
| >5-fold | 0 | 0 | 1 |
|  | 84 | 17 | 4 |
| Total = 105 controls |  |  |  |
| Odd ratios for recurrence[c] | 1.0 | 1.8[d] | 9.5[e] |

The odds ratios for gene amplification were:

| Gene copy | OR | 95% confidence interval | P |
|---|---|---|---|
| 1 | 1.00 | Not applicable | NA |
| 3–5 | 1.89 | 0.493–7.252 | 0.3530 |
| >5 | 14.79 | 1.93–113.347 | 0.0095 |

Single copy compared to any amplification was as follows: $X^2 = 14.35$ (2 d.f.), P = 0.00077. The predictive value of gene amplification compared with expression for outcome (recurrence) was P = 011; vise versa P = 0.055. NA, not applicable.
[a]Gene amplification was also a significant predictor of recurrence.
[b]Since the quality of DNA obtained from paraffin-embedded tissue is variable, only gene copy levels increased by 3-fold or greater were regarded as consistently distinguishable from single copy. A cutoff of 2-fold has been used for DNA from frozen tissue.
[c]Odds. ratios for recurrence ($X^2 = 15.75$, 2 d.f., P = 0.0004). Trend test ($X^2 = 14.70$, 1 d.f., P = 0.0001). Odds ratios for recurrence for any overexpression ("intermediate" plus "high" immunostaining) is 3.0 with 95% confidence interval of 1.5 to 6.1 ($X^2 = 10.46$, P = 0.0012).
[d]95% confidence limits, 0.81 to 4.1.
[e]95% condifence limits, 2.2 to 42.0.

Statistical analysis of the data demonstrate an OR (approximately equivalent to relative risk) of 3.0 for developing recurrent breast cancer in patients with any level of overexpression of HER-2/neu compared to those whose malignancies expressed normal levels (odds ratio, 3.0; 95% confidence limits, 1.5 and 6.1; $X^2=10.46$ on 1 d.f., P=0.0012).

Increasing levels of HER-2/neu gene amplification in these carcinomas were also associated with an increased risk of recurrent breast cancer ($X^2=14.35$ on 2 d.f., P=0.0008; $X^2$ for trend=3.59 on 1 d.f., P=0.0002). For given expression levels based on immunostaining status, determination of DNA amplification level added only marginal additional prognostic information ($X^2=2.58$ on 1 d.f., P=0.11) . Conversely, for known DNA amplification level, HER-2/neu expression based on immunostaining added more information although formal statistical significance was not achieved ($X^2=3.69$ on 1 d.f., P=0.055).

It is evident from the above results that the subject methodology provides for a powerful capability in determining a wide variety of components in cells on an individual cell basis. By using computerized image analysis and staining of tissue samples or fixed dispersed cells, one can obtain a determination of one or more components of cells, providing for prognostic significance in cases of disease, or establishing a better understanding of physiological processes and the interactions of the individual cellular components in providing for proliferation, differentiation, and function.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for quantitating a surface membrane or cytosol protein, said method comprising:
   (1) staining immobilized fixed cells with a labeled binding composition comprising a probe binding specifically to said surface membrane or cytosol protein, wherein said label can be quantitated by computerized image analysis;
   (2) determining the signal value from a known number of said fixed cells by means of computerized image analysis; and
   determining the amount of said surface membrane or cytosol protein per cell by comparing said signal value obtained from said fixed cells with control values between control cellular compositions having said surface membrane or cytosol protein at different cellular amounts for which signal values are obtained in accordance with steps (1) and (2) and for which the amount of said surface membrane or cytosol protein for a known number of cells is obtained by an alternative method of analysis other than computerized image analysis.

2. A method according to claim 1, wherein said label is an enzyme.

3. A method, for quantitating a molecular cellular component, said method comprising:
   (1) staining immobilized fixed cells with a labeled binding composition comprising a probe binding specifically to said molecular cellular component, wherein said label can be quantitated by computerized image analysis:
   (2) determining the signal value from a known number of said fixed cells by means of computerized image analysis: and
   determining the amount of said molecular cellular component per cell by comparing said signal value obtained from said fixed cells with control values between control cellular compositions having said molecular cellular component at different cellular amounts for which signal values are obtained in accordance with steps (1) and (2) and for which the amount of said molecular cellular component for a known number of cells is obtained by an alternative method of analysis other than computerized image analysis, wherein said alternative method of analysis comprises comparing the value obtained from analysis of lysates of said control cellular compositions as compared to the value obtained with pure preparations of said molecular cellular component using the same method of analysis.

4. A method according to claim 3, wherein said alternative method comprises gel electrophoresis of said lysate and said pure preparations, wherein said molecular cellular component in said lysate and pure preparations is labeled and comparing the signals obtained from the resulting bands of said gel electrophoresis.

5. A method according to claim 1, wherein said cells are tumor cells and said surface membrane or cytosol protein is the protein product of an oncogene.

6. A method according to claim 3, wherein said control cellular compositions comprise cells modified by introduction of an expression construct comprising a gene encoding said cellular protein.

7. A method for quantitating HER-2/neu protein from breast cancer tissue as a prognostic of relapse, said method comprising:

(1) staining fixed cells from said breast cancer tissue with an enzyme labeled binding composition comprising a probe binding specifically to said HER-2/neu protein, wherein said label can be quantitated by computerized image analysis;

(2) determining the signal value from a known number of said fixed cells by means of computerized image analysis; and determining the amount of said HER-2/neu protein per cell by comparing said signal value obtained from said fixed cells with control values between control cellular compositions having said HER-2/neu protein at different cellular amounts for which signal values are obtained in accordance with steps (1) and (2) and for which the amount of said HER-2/neu protein for a known number of cells is obtained by comparing the value obtained from analysis of lysates of said control cellular compositions as compared to the value obtained with pure preparations of said HER-2/neu protein using the same alternative method of analysis other than computerized image analysis.

8. A kit comprising at least three immortalized cell lines comprising differing amounts of a surface membrane protein or cytosol protein, wherein said immortalized cell lines comprise at least one naturally occurring tumor cell composition; and an antibody composition that specifically binds to said surface membrane protein or cytosol protein.

9. A kit according to claim 8, wherein said surface membrane protein or cytosol protein is the protein product of an oncogene.

10. A kit according to claim 9, wherein said oncogene is HER-2/neu.

11. A kit according to claim 8, wherein said cell lines are fixed to a solid support.

12. A method according to claim 3, wherein said labeled binding composition is an enzyme conjugated antibody.

* * * * *